United States Patent
Guan et al.

(10) Patent No.: US 9,824,297 B1
(45) Date of Patent: Nov. 21, 2017

(54) METHOD AND APPARATUS FOR MEDICATION IDENTIFICATION

(71) Applicant: AIC Innovations Group, Inc., New York, NY (US)

(72) Inventors: Lei Guan, Philadelphia, PA (US); Adam Hanina, New York, NY (US); Gordon Kessler, Mount Kisco, NY (US)

(73) Assignee: AIC Innovations Group, Inc., New York, NY (US)

( * ) Notice: Subject to any disclaimer, the term of this patent is extended or adjusted under 35 U.S.C. 154(b) by 360 days.

(21) Appl. No.: 14/044,363

(22) Filed: Oct. 2, 2013

(51) Int. Cl.
*G06K 9/00* (2006.01)
*G06K 9/62* (2006.01)
*G06K 9/66* (2006.01)

(52) U.S. Cl.
CPC .............. *G06K 9/6202* (2013.01); *G06K 9/66* (2013.01)

(58) Field of Classification Search
CPC ............................... G06K 9/6202; G06K 9/66
USPC .................................................. 382/128, 154
See application file for complete search history.

(56) References Cited

U.S. PATENT DOCUMENTS

| | | |
|---|---|---|
| 3,814,845 A | 6/1974 | Hurlbrink et al. |
| 5,065,447 A | 11/1991 | Barnsley et al. |
| 5,441,047 A | 8/1995 | David et al. |
| 5,544,649 A | 8/1996 | David et al. |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brudny et al. |
| 5,911,132 A | 6/1999 | Sloane |
| 5,961,446 A | 10/1999 | Beller et al. |
| 6,151,521 A | 11/2000 | Guo et al. |
| 6,233,428 B1 | 5/2001 | Fryer |
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2 | 11/2002 | Martin et al. |
| 6,535,637 B1 | 3/2003 | Wootton et al. |

(Continued)

OTHER PUBLICATIONS

Danya International, Inc., *Pilot Study Using Cell Phones for Mobile Direct Observation Treatment to Monitor Medication Compliance of TB Patients*, Mar. 20, 2009, www.danya.com/MDOT.asp.

(Continued)

*Primary Examiner* — Tom Y Lu
(74) *Attorney, Agent, or Firm* — Fish & Richardson P.C.

(57) ABSTRACT

A system and method for recognizing a medication are provided. The method includes the steps of presenting a medication to a medication identification apparatus, the medication identification apparatus adapted to visually image the presented medication and visually imaging the presented medication. A predetermined transformation may be applied to the visually imaged presented medication, the predetermined transformation adjusting one or more parameters of the visually imaged presented medication along one or more dimensions. Finally, the transformed visually imaged medication is compared to a medication library to determine a closest match therebetween.

20 Claims, 4 Drawing Sheets

(56) References Cited

U.S. PATENT DOCUMENTS

| | | | |
|---|---|---|---|
| 6,611,206 | B2 | 8/2003 | Milanski et al. |
| 6,705,991 | B2 | 3/2004 | Bardy |
| 6,879,970 | B2 | 4/2005 | Shiffman et al. |
| 6,988,075 | B1 | 1/2006 | Hacker |
| 7,184,047 | B1 | 2/2007 | Crampton |
| 7,184,075 | B2 | 2/2007 | Reiffel |
| 7,256,708 | B2 | 8/2007 | Rosenfeld et al. |
| 7,277,752 | B2 | 10/2007 | Matos |
| 7,304,228 | B2 | 12/2007 | Bryden et al. |
| 7,307,543 | B2 | 12/2007 | Rosenfeld et al. |
| 7,317,967 | B2 | 1/2008 | DiGianfilippo et al. |
| 7,340,077 | B2 | 3/2008 | Gokturk |
| 7,395,214 | B2 | 7/2008 | Shillingburg |
| 7,415,447 | B2 | 8/2008 | Shiffman et al. |
| 7,448,544 | B1 | 11/2008 | Louie et al. |
| 7,562,121 | B2 | 7/2009 | Berisford et al. |
| 7,627,142 | B2 | 12/2009 | Kurzweil et al. |
| 7,657,443 | B2 | 2/2010 | Crass et al. |
| 7,692,625 | B2 | 4/2010 | Morrison et al. |
| 7,747,454 | B2 | 6/2010 | Bartfeld et al. |
| 7,761,311 | B2 | 7/2010 | Clemets et al. |
| 7,769,465 | B2 | 8/2010 | Matos |
| 7,774,075 | B2 | 8/2010 | Lin |
| 7,874,984 | B2 | 1/2011 | Elsayed et al. |
| 7,881,537 | B2 | 2/2011 | Ma et al. |
| 7,908,155 | B2 | 3/2011 | Fuerst et al. |
| 7,912,733 | B2 | 3/2011 | Clements et al. |
| 7,956,727 | B2 | 6/2011 | Loncar |
| 7,983,933 | B2 | 7/2011 | Karkanias et al. |
| 8,321,284 | B2 | 11/2012 | Clemets et al. |
| 8,448,846 | B2 * | 5/2013 | Needhan ............ G06F 19/3456 235/375 |
| 9,008,411 | B2 * | 4/2015 | DeLise, Jr. ........... G06F 19/326 348/135 |
| 2001/0049673 | A1 | 12/2001 | Dulong et al. |
| 2001/0056358 | A1 | 12/2001 | Dulong et al. |
| 2002/0026330 | A1 | 2/2002 | Klein |
| 2002/0093429 | A1 | 7/2002 | Matsushita et al. |
| 2002/0143563 | A1 | 10/2002 | Hufford et al. |
| 2003/0164172 | A1 | 9/2003 | Chumas et al. |
| 2003/0190076 | A1 | 10/2003 | Delean |
| 2003/0225325 | A1 | 12/2003 | Kagermeier et al. |
| 2004/0100572 | A1 | 5/2004 | Kim |
| 2004/0107116 | A1 | 6/2004 | Brown |
| 2004/0155780 | A1 | 8/2004 | Rapchak |
| 2005/0144150 | A1 | 6/2005 | Ramamurthy et al. |
| 2005/0149361 | A1 | 7/2005 | Saus et al. |
| 2005/0180610 | A1 | 8/2005 | Kato et al. |
| 2005/0182664 | A1 | 8/2005 | Abraham-Fuchs et al. |
| 2005/0234381 | A1 | 10/2005 | Niemetz et al. |
| 2005/0267356 | A1 | 12/2005 | Ramasubramanian et al. |
| 2006/0066584 | A1 | 3/2006 | Barkan |
| 2006/0218011 | A1 | 9/2006 | Walker et al. |
| 2006/0238549 | A1 | 10/2006 | Marks |
| 2007/0008112 | A1 | 1/2007 | Covannon et al. |
| 2007/0008113 | A1 | 1/2007 | Spoonhower et al. |
| 2007/0030363 | A1 | 2/2007 | Cheatle et al. |
| 2007/0118389 | A1 | 5/2007 | Shipon |
| 2007/0194034 | A1 | 8/2007 | Vasiadis |
| 2007/0233035 | A1 | 10/2007 | Wehba et al. |
| 2007/0233049 | A1 | 10/2007 | Wehba et al. |
| 2007/0233050 | A1 | 10/2007 | Wehba et al. |
| 2007/0233281 | A1 | 10/2007 | Wehba et al. |
| 2007/0233520 | A1 | 10/2007 | Wehba et al. |
| 2007/0233521 | A1 | 10/2007 | Wehba et al. |
| 2007/0273504 | A1 | 11/2007 | Tran |
| 2008/0000979 | A1 | 1/2008 | Poisner |
| 2008/0093447 | A1 | 4/2008 | Johnson et al. |
| 2008/0114226 | A1 | 5/2008 | Music et al. |
| 2008/0114490 | A1 | 5/2008 | Jean-Pierre |
| 2008/0138604 | A1 | 6/2008 | Kenney et al. |
| 2008/0140444 | A1 | 6/2008 | Karkanias et al. |
| 2008/0162192 | A1 | 7/2008 | Vonk et al. |
| 2008/0178126 | A1 | 7/2008 | Beeck et al. |
| 2008/0201174 | A1 | 8/2008 | Ramasubramanian et al. |
| 2008/0219493 | A1 | 9/2008 | Tadmor |
| 2008/0275738 | A1 | 11/2008 | Shillingburg |
| 2008/0290168 | A1 | 11/2008 | Sullivan et al. |
| 2008/0297589 | A1 | 12/2008 | Kurtz et al. |
| 2008/0303638 | A1 | 12/2008 | Nguyen et al. |
| 2009/0012818 | A1 | 1/2009 | Rodgers |
| 2009/0018867 | A1 | 1/2009 | Reiner |
| 2009/0043610 | A1 | 2/2009 | Nadas et al. |
| 2009/0048871 | A1 | 2/2009 | Skomra |
| 2009/0095837 | A1 | 4/2009 | Lindgren |
| 2009/0128330 | A1 | 5/2009 | Monroe |
| 2009/0159714 | A1 | 6/2009 | Coyne, III et al. |
| 2009/0217194 | A1 | 8/2009 | Martin et al. |
| 2009/0245655 | A1 | 10/2009 | Matsuzaka |
| 2010/0042430 | A1 | 2/2010 | Bartfield |
| 2010/0050134 | A1 | 2/2010 | Clarkson |
| 2010/0057646 | A1 | 3/2010 | Martin et al. |
| 2010/0092093 | A1 | 4/2010 | Akatsuka et al. |
| 2010/0136509 | A1 | 6/2010 | Mejer et al. |
| 2010/0138154 | A1 | 6/2010 | Kon |
| 2010/0255598 | A1 | 10/2010 | Melker |
| 2010/0262436 | A1 | 10/2010 | Chen et al. |
| 2010/0316979 | A1 | 12/2010 | Von Bismarck |
| 2011/0021952 | A1 | 1/2011 | Vallone |
| 2011/0119073 | A1 | 5/2011 | Hanina et al. |
| 2011/0153360 | A1 | 6/2011 | Haninia et al. |
| 2011/0161109 | A1 | 6/2011 | Pinsonneault et al. |
| 2011/0195520 | A1 | 8/2011 | Leider et al. |
| 2011/0275051 | A1 | 11/2011 | Hanina et al. |
| 2012/0075464 | A1 | 3/2012 | Derenne et al. |
| 2013/0287294 | A1 * | 10/2013 | Ye ........................ G06T 15/04 382/154 |

OTHER PUBLICATIONS

University of Texas, *GuideView*, Mar. 15, 2007, http://www.sahs.uth.tmc.edu/MSriram/GuideView/.

Chen, Pauline W., *Texting as a Health Tool for Teenagers*, The New York Times, Nov. 5, 2009, http://www.nytimes.com/2009/11/05/health/05chen.html?_r=1&emc=.

Whitecup, Morris S., *2008 Patient Adherence Update: New Approaches for Success*, Guideline Trend Report, Oct. 2008.

Osterberg, Lars and Blaschke, Terrence, *Adherence to Medication*, New England Journal of Medicine 2005; 353:487-97, Aug. 4, 2005.

"Global Tuberculosis Control: A short update to the 2009 report", *World Health Organization*, (2009).

"Super-Resolution", *Wikipedia*, (Oct. 5, 2010).

Non-Final Office Action from PTO, U.S. Appl. No. 12/620,686, (dated Dec. 21, 2011), 1-78.

Final Office Action from PTO, U.S. Appl. No. 12/620,686, (dated May 8, 2012), 1-24.

Non-Final Office Action from PTO, U.S. Appl. No. 13/558,377, (dated Oct. 22, 2012), 1-21.

Final Office Action from PTO, U.S. Appl. No. 13/558,377, dated May 7, 2013, 1-29.

PCT Search report and written opinion, (PCT/US2010/56935, (dated Jan. 12, 2011),1-9.

International Preliminary Report on Patentability, (PCT/US2010/056935) (dated May 31, 2012), 1-8.

Non-Final Office Action from PTO, U.S. Appl. No. 12/646,383, (dated Dec. 22, 2011),1-78.

Final Office Action from PTO, U.S. Appl. No. 12/646,383, (dated May 8, 2012), 1-31.

Non-Final Office Action from PTO, U.S. Appl. No. 13/558,380, (dated Oct. 4, 2012), 1-20.

Wang et al. "Recent Developments in human motion analysis." Pattern Recognition 36 (220) 585-601 (Nov. 2001).

Final Office Action from PTO, U.S. Appl. No. 13/588,380, (dated Mar. 1, 2013), 1-27.

Non-Final Office Action from PTO, U.S. Appl. No. 12/646,603, (dated Oct. 13, 2011),1-74.

Final Office Action from PTO, U.S. Appl. No. 12/646,603, (dated Feb. 1, 2012), 1-17.

Non-Final Office Action from PTO, U.S. Appl. No. 12/646,603, (dated Jun. 13, 2013), 1-16.

(56) References Cited

OTHER PUBLICATIONS

Non-Final Office Action from PTO, U.S. Appl. No. 12/728,721, (dated Jan. 6, 2012), 1-31.
Final Office Action from PTO, U.S. Appl. No. 12/728,721, (dated Apr. 12, 2012), 1-31.
Non-Final Office Action from PTO, U.S. Appl. No. 12/728,721, (dated May 9, 2013), 1-25.
Non-Final Office Action from PTO, U.S. Appl. No. 12/815,037, (dated Mar. 28, 2012),1-17.
Final Office Action from PTO, U.S. Appl. No. 12/815,037, (dated Sep. 13, 2012), 1-15.
Non-Final Office Action from PTO, U.S. Appl. No. 12/815,037, (dated Jul. 18, 2013), 1-19.
PCT Search report and written opinion, (PCT/US2011/35093) (dated Sep. 12, 2011),1-8.
Non-Final Office Action from PTO, U.S. Appl. No. 12/899,510, (dated Jan. 23, 2013), 1-20.
Final Office Action from PTO, U.S. Appl. No. 12/899 510, (dated Aug. 20, 2013).
PCT Search report and written opinion, (PCT/US11/54666), (dated Feb. 28, 2012), 1-13.
Non-Final Office Action from PTO, U.S. Appl. No. 12/898,338, (dated Jun. 19, 2012), 1-16.
Final Office Action from PTO, U.S. Appl. No. 12/898,338, dated Nov. 9, 2012), 1-12.
PCT Search report and written opinion, (PCT/US11/54668) dated Feb. 28, 2012, 1-12.
Non-Final Office Action from PTO, U.S. Appl. No. 13/189,518, (dated Dec. 21, 2012), 1-10.
Final Office Action from PTO, U.S. Appl. No. 13/189,518, (dated Jul. 23, 2013), 1-16.
PCT Search report and written opinion, (PCT/US12/41785), (dated Aug. 17, 2012),1-10.
Non-Final Office Action from PTO, U.S. Appl. No. 13/235,387, dated Sep. 12, 2013), 1-16.
PCT Search report and written opinion, (PCT/US12/42843), (dated Aug. 31, 2012), 1-8.
PCT Search report and written opinion, (PCT/US2012/051554), (dated Oct. 19, 2012), 1-12.
Huynh et al., "Real time detection, tracking and recognition of medication intake." World Academy of Science, Engineering and Technology 60 (2009), 280-287.
PCT Search report and written opinion, (PCT/US12/59139) (dated Dec. 18, 2012), 1-15.
PCT Search report and written Opinion, (PCT/US13/20026), (dated Aug. 5, 2013), 1-14.
Ammouri, S.; Biloduau, G.-A, "Face and Hands Detectionand Tracking Applied to the Monitoring of Medication Intake," Computer and Robot Vision, 2008. CRV '08. Canadian Conference on, vol. No., pp. 147, 154, May 28-30, 2008.
Batz, et al. "A computer Vision System for Monitoring Medicaiton Intake," in Proc. IEEE 2nd Canadian Conf. on Computer and Robot Vision, Victoria, BC, Canada, 2005, pp. 362-369.
Valin, et al. "Video Surveillance of Medication intake", Int. Conf. of the IEEE Engineering in Medicine and Biology Society, New York City, USA, Aug. 2006.
Bilodeau et al. Monitoring of Medication Intake Using a Camera System. Journal of Medical Systems 2011. [retrieved on Feb. 18, 2013] Retrieved from ProQuest Technology Collection.
Mintchell, "Exploring the Limits of Machine Vision", Automating World, Oct. 1, 2011.

\* cited by examiner

METHOD AND APPARATUS FOR MEDICATION IDENTIFICATION

FIELD

This invention relates generally to recognition of medication, and more particularly to an apparatus and method for the medication recognition for use with a medication monitoring system employing video capture, allowing for a diverse set of medication to be recognized with minimal additional system training required for each medication.

BACKGROUND

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. As has been shown in regards to various public health medication administration situations, such as administration of tuberculosis medication by the WHO, Directly Observed Treatment (DOT) improves compliance of patients. *Global Tuberculosis Control: A Short Update to the* 2009 *Report*, World Health Organization, 2009. As is shown in this report, funding for implementing DOT programs is high. Thus, the ability to implement such a program with less of a financial burden would be desirable.

The total healthcare cost of drug-related morbidity, including poor adherence, is estimated at $290 billion per year in the US. Treatment of patients with poor adherence can require twice the resources from the healthcare system than treatment of more compliant individuals. Mortality and morbidity rates are much higher for patients who do not follow their prescribed drug therapy, especially for patients suffering from a chronic illness. Currently, 75% of healthcare spending in the US is directed towards treatment of chronic disease. These same chronically ill patients who are also non-adherent to their medication prescriptions are twice as likely to be hospitalized. Low levels of medication adherence also contribute to the high costs of clinical trials. In the US, patient recruitment is estimated at $6533 per individual and up to three times that amount to replace someone who has left. As a result, the number of clinical trials conducted abroad has been increasing. By 2012, an estimated 65% of FDA-regulated clinical trials will be conducted outside of the US, raising issues around regulation and supervision.

Dr Lars Osterberg, M.D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series,* 2008 *Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. Similar failure to adhere to medication prescriptions plagues the population health management field. It is against this backdrop of poor adherence, and potential danger to patients, that the present invention operates.

Traditional monitoring methods have problems with reliability and cost, and may place a substantial burden on the patient. Pill counting and patient interviews are unreliable ways of measuring medication adherence, as is evidenced in the above studies, as they offer no information on the time of day medication is taken or whether the patient has skipped doses entirely. Self-reporting by individuals, even employing ePRO diaries, IVRS or web portal communications have also been shown to be untrustworthy as many patients fail to record accurate data. Technologically advanced solutions, such as digital pill container caps and smart packaging report only when the patient has opened the medication container and cannot confirm medication administration. Smart pills, while accurate, are expensive, require a modification to the manufacturing process, and are inconvenient for the patient. Even if patients are not intentionally deceptive, barriers to medication adherence such as the perceived impact of a medicine, knowledge about illness, forgetfulness, or lack of social support, are contributing factors to why 75% of Americans do not take their medicine as prescribed.

An extremely effective way to confirm medication adherence is through direct observation. The WHO's Directly Observed Treatment, short course (DOTs) program has radically improved overall compliance rates of TB patients. Indeed, such direct observation is typically employed in phase 1 clinical trials, where assurance of adherence is critical. Unfortunately, the labor-intensive nature of the program—hiring care workers to directly monitor patients— is expensive, and places a substantial burden on the patient. [AI Cure Technologies will provide an automated virtual direct observation solution, AiView™ that may be applied to larger populations for a fraction of the cost of DOTs. AiView™ will leverage the increasing familiarity and access to webcam-enabled devices by incorporating a gesture and object recognition monitoring platform.] Traditionally, participants attend introductions and follow ups for clinical trials, or in other disease management situations, in-person. Once the initial start up has been performed, however, patients are typically on their own to confirm that they are properly taking their medication. Infrequent checkups, typically every few weeks or longer, have proven to be insufficient. A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant. Similarly, there is no mention of non-pill based medications. Furthermore, there is an assumption that a medication has been already trained to be recognized by the system, an assumption that may cause a problem given the number of different possible medications, including generic medications, that may be taken by an individual in accordance with a particular prescription.

Therefore, it would be desirable to provide an apparatus that overcomes the drawbacks of the prior art.

SUMMARY

In U.S. patent application Ser. No. 12/620,686, filed Nov. 18, 2009, titled Method and Apparatus for Verification of Medication Administration Adherence, abandoned; U.S. patent application Ser. No. 13/558,377, filed Jul. 26, 2012, titled Method and Apparatus or Verification of Medication Administration Adherence, currently pending; U.S. patent application Ser. No. 12/646,383, filed Dec. 23, 2009, titled Method and Apparatus for Verification of Clinical Trial Adherence, abandoned; U.S. patent application Ser. No. 13/558,380, filed Jul. 26, 2012, titled Method and Apparatus for Verification of Clinical Trial Adherence, currently pending; U.S. patent application Ser. No. 12/646,603, filed Dec. 23, 2009, titled Method and Apparatus for Management of Clinical Trials, currently pending; U.S. patent application Ser. No. 12/728,721, filed Mar. 22, 2010, titled Apparatus and Method for Collection of Protocol Adherence Data, currently pending; U.S. patent application Ser. No. 12/815,037, filed Jun. 14, 2010, titled Apparatus and Method for Recognition of Patient Activities when Obtaining Protocol Adherence Data, currently pending; U.S. patent application Ser. No. 13/189,518, filed Jul. 24, 2011, titled Method and Apparatus for Monitoring Medication Adherence, currently pending; U.S. patent application Ser. No. 13/235,387, filed Sep. 18, 2011, titled Apparatus and Method for Recognition of Patient Activities, currently pending; U.S. patent application Ser. No. 13/674,209, filed Nov. 12, 2012, titled Method and Apparatus for Identification, currently pending; and U.S. patent application Ser. No. 13/674,459, filed Nov. 12, 2012, titled Method and Apparatus for Recognition of Inhaler Actuation, currently pending; the contents of these applications being incorporated herein by reference, the inventors of the present invention have proposed a system, method and apparatus that allow for complete control and verification of adherence to a prescribed medication protocol or machine or apparatus use in a clinical trial or disease management setting, whether in a health care provider's care, or when self administered in a homecare situation by a patient.

These applications present the only medication management system that may determine whether a user is actually following a protocol, including properly determining whether the user has ingested their medication, such as by placing the medication in their mouth or the like, in real time, provide additional assistance in real time to a user, starting with instructions, such as audio and/or video/visual instructions, and the like, and moving up to contact from a medication administrator if it is determined that the user would need or benefit from such assistance in any medical adherence situation, including clinical trial settings, home care settings, healthcare administration locations, such as nursing homes, clinics, hospitals and the like, and in clinical trial settings. Additional training may be provided in accordance with the real-time feedback so that the user can be further assisted in properly performing steps associated with proper medication adherence.

The inventive solution, in accordance with one or more embodiments of the present invention, recognizes the need to be able to apply the above described system in a great number of scenarios where knowledge of the visual characteristics of the medication to be taken may not be known, or where the number of medications to be monitored by the system may be very large, and where no special hardware is to be employed in the system calibration process, or during use in the medication recognition process, such as a color chart, special tray or medication holder or the like. In accordance with one or more embodiments of the present invention, a reference library of medications is trained to the system. These medications may be selected as to their popularity or as covering a wide gamut of possible medication characteristics. These characteristics may be defined in any number of dimensions, and may include color, shape, surface reflectivity, surface markings, relationship between any number of these characteristics, etc.

These medications may then be trained so that the system is adapted to recognize and differentiate between these various medications. Such training may be performed in accordance with one or more known methods. Once trained, if a user is prescribed one of the trained medications, the system will recognize whether the user presents the prescribed medication to the system (as noted in one or more of the above-note applications). If, however, a medication is prescribed that has not been trained into the system, or if the user is to take a generic medication having a yet unknown set of visual characteristics, it is not practicable to train the system for each such scenario.

In such a situation, the user may be asked to perform a mini-training process with the system. The user may be asked to show the medication to an imaging camera of the system in a predetermined sequence. The user may also be asked to perform a particular gesture or set of gestures or predetermined steps with the medication. The system may turn on lights, etc. at different times of the mini-training process. Such lights may be employed to change the illumination of a medication or environment, or may be used to change a color of the environment, either alone or in sequence, to aid in a more accurate calibration and/or identification process. In such a scenario, the system is designed to determine one or more differences along one or more dimensions between the current medication subject to the mini-training process and one or more of the medication previously trained on the system. Therefore, rather than requiring a complete training process for each medication, only a difference along one or more dimensions need be determined. These determined differences along the one or more dimensions are then preferably stored to be applied in the future as a transformation definition.

Once such a transformation definition is stored, when using a system requiring identification of a medication, the user may show the medication to be administered to an imaging device of the monitoring system, and may be asked to perform one or more actions similar to those performed in accordance with the training regimen noted above. The system, upon capturing one or more images of the medication and any other images performed by the user, may then apply the transformation definition, and then after applied, compare and classify the transformed image. It is intended that if the transformation definition is properly stored and defined, the transformed image should then correspond to the previously identified closest trained medication. Alternatively, if the medication to be administered is known, the transformation may be performed on the stored image data, thus producing a transformed reference image. Then this transformed image may be compared to the captured image.

Additionally, it is contemplated in accordance with one or more embodiments of the invention, one or more environmental factors, such as lighting or the like, may be provided as an input into the transformation definition, thus aiding in modifying the transformation definition according to the one or more environmental factors so that the transformed images are likely to result in better and closer matches to the one or more trained medications. Furthermore, imaging of the medication may be performed, as noted above, while a particular gesture or other medication administration steps are performed so that proper medication identification can be performed. Particular motions in response to the required gestures may be used to identify the user, and may be used to classify the input images further. Any unique motions may be employed to further identify a user in the future, and may also be used to help identify medication, as will be described below.

Therefore, a method and system are provided allowing for proper identification of medication without the need for exhaustive training of each and every medication to be recognized.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION

Figure 1:
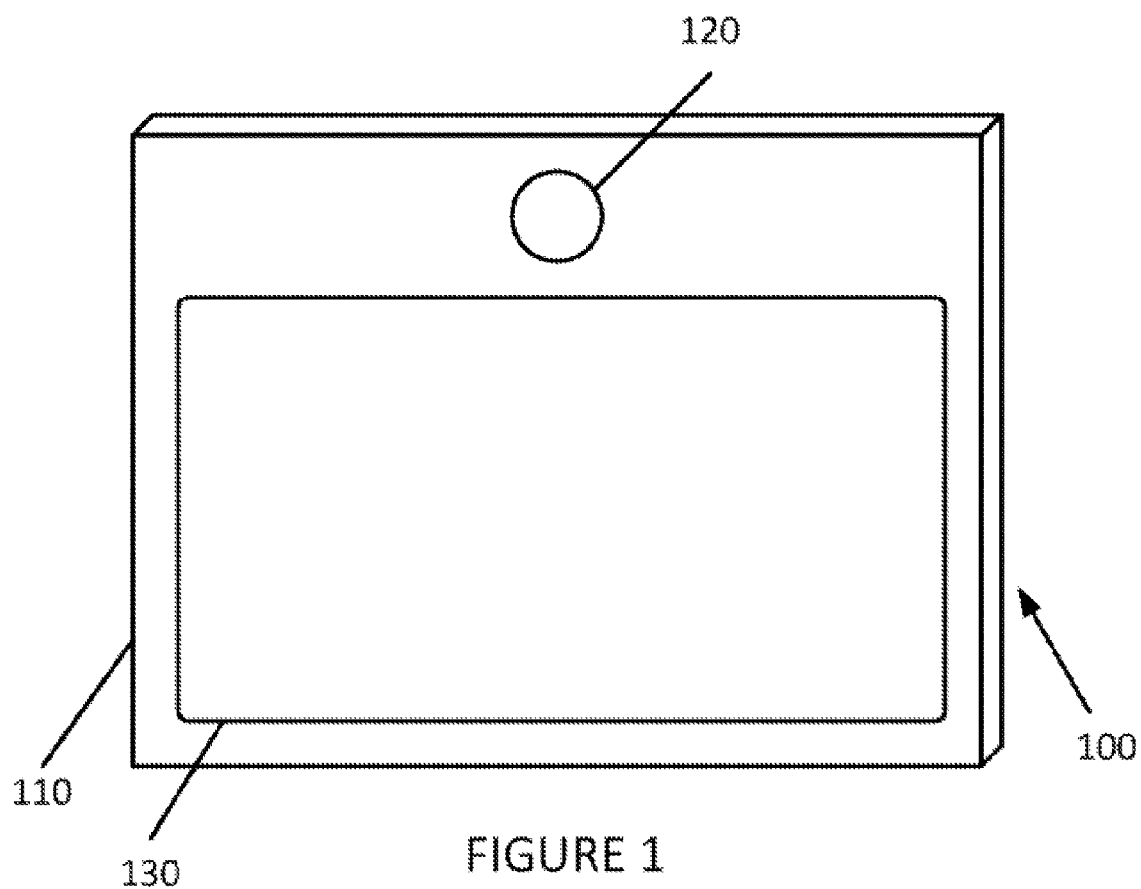
FIG. 1 depicts a medication recognition apparatus constructed in accordance with an embodiment of the invention.

The invention will now be described making reference to the following drawings in which like reference numbers denote like structure or steps. Referring first to FIG. 1, a display and image capture apparatus 100 that may be employed in accordance with one or more embodiments of the present invention for acquiring one or more images, and for displaying the one or more images and additional material, for performing processing in accordance with the various embodiments of the invention, and for storing computer program instructions, acquired data, and other information on a non-volatile computer readable storage medium is shown. Apparatus 100 preferably includes a housing 110, an image capture camera 120 and a display 130. Image capture camera 120 may comprise a single camera element, a stereo camera element or other appropriate image capture device. Other elements, as known to one of ordinary skill in the art, including ports, power attachments, processors for processing data, and the like may also be provided in accordance with apparatus 100. Apparatus 100 may comprise a computer, tablet computer, mobile device, or any other appropriate computing device including a camera, processor and memory.

It is further contemplated in accordance with the various embodiments of the invention that apparatus may include one or more self-check mechanisms, including mechanisms for determining proper ambient light, direction and background of the camera and the background imaged by the camera, or other environmental issues that may be improved to further aid in the imaging of any images by apparatus 100. Additionally, if at any time it is determined that lighting conditions are too difficult for imaging apparatus 100, it may be possible to provide a light burst from a strobe or display to aid in illuminating the images to be captured. This light burst may come from a dedicated light, or the display of the image capture apparatus, and may further be provided in one or more colors, in sequence or alone, to further aid in determining color or other identifying characteristics of a medication pill or the like. The above descriptions of the various embodiments of the invention will assume that such a display and image capture apparatus 100 may be employed. The invention, however, shall not be so limited and may be employed on any structure of image capture camera and display, whether contained in a single or multiple apparatuses, or any other appropriate system for capturing images and providing processing as described above. Furthermore, it is contemplated in accordance with the invention that image capture and processing may be implemented in a cloud computing environment, with an image capture device forwarding captured images to a remote location for storage and processing. Responses contemplated in accordance with the above description may be provided to the image capture device in manners known to those of ordinary skill in the art.

Figure 2:
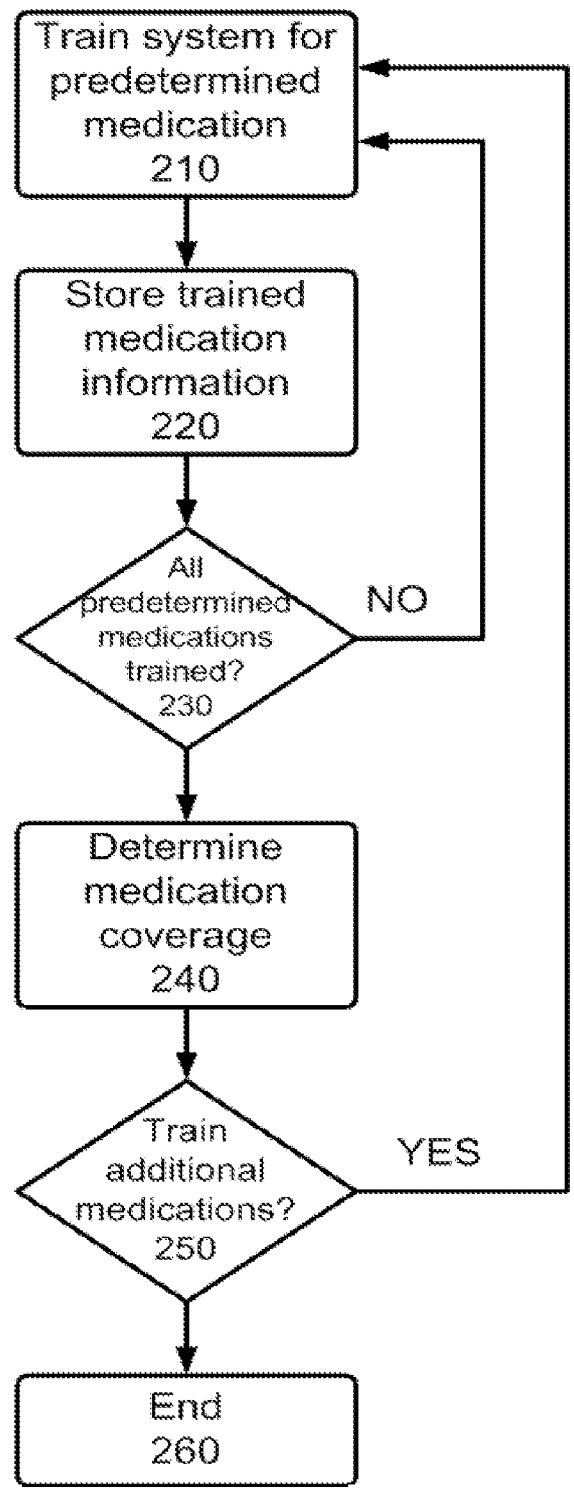
FIG. 2 is a flowchart diagram depicting training employing the system of the invention for training a plurality of predefined medications in accordance with an embodiment of the invention.

Referring next to FIG. 2, a high level flowchart describing functionality in accordance with one or more embodiments of the system is shown. As is shown in FIG. 2, during a training session, processing begin at step 210 in which a first predetermined medication is trained to be recognized by the system. One or more known methods and systems for such training may be employed, including but not limited to feature extraction, supervised learning and the like. Such training may also employ a combination of 2D and 3D scanning techniques. The stored training data may comprise one or more images or video taken of a medication in one or more scenarios. These images or other training data may be preprocessed, such as by modifying color, modifying highlights, shadows, etc., cropping images to better present relevant portions thereof, the cropping being performed manually or automatically through feature recognition or other process. The medication may also be labeled and/or confirmed to be a correct medication. Medication packaging, barcoding or other identification information may also be imaged to further confirm the precise identity of the medication being trained. Other sources of medication identification may also be employed These reference medications may also be generated by scanning medication substitutes, such as plastic versions of pills, or using other identifying data to allow for a reference set of medications to be provided. Color changes, shape transformations and the like may also be employed. Further textual or other information may be provided from a pill bottle or the like, and may be stored with the pill image. Reference libraries may also be accessed to further provide color calibration or other medication characteristics once the identity of the pill has been determined. Such a reference set of images may also be set up from existing databases of pill images, and be tuned through the application of the system over time, as will be described below.

After training, the training data, either in original format and/or after being modified, is stored to a storage medium at step 220. As described above, this storage medium may be on a local device, at a remote storage location for processing, or the like. After storing the training data for a particular medication, at step 230 it is determined whether all predetermined medications have been trained. If not, processing returns to step 210 for processing of further medications.

If at step 230 it is determined that all predetermined medications have been trained, then processing may proceed to step 240 where a determination may be made as to whether the set of predetermined medications sufficiently covers the spectrum of possible medications along one or more relevant dimensions. Alternatively processing may stop after step 230. Once determined, at step 250 it is questioned whether additional medications should be trained to sufficiently cover a spectrum of possible medications. If yes, processing returns to step 210 for training of further medications. If no, then processing ends.

Figure 3:
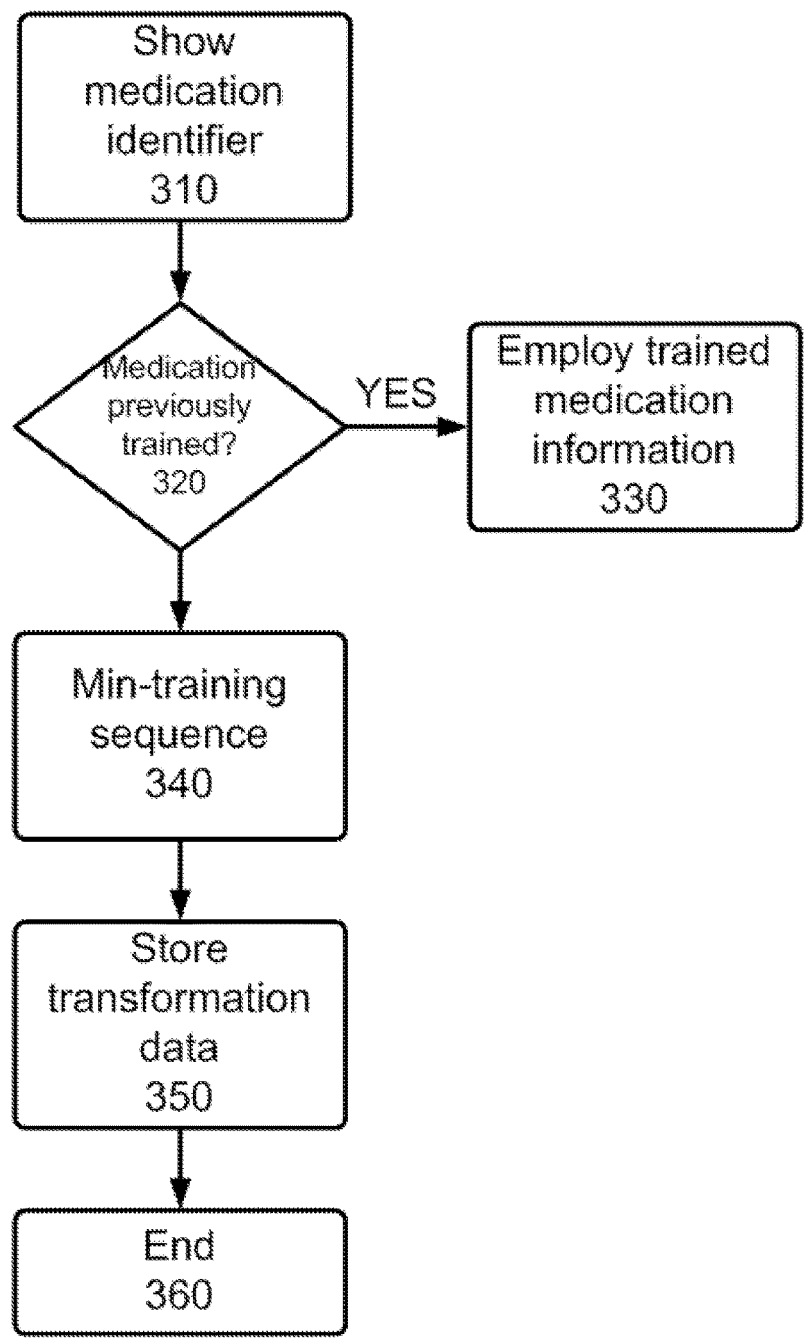
FIG. 3 is a flowchart diagram depicting training for a medication that is not one of the predefined medications in accordance with an embodiment of the invention.

After training of the predetermined medications, FIG. 3 depicts an exemplary mini-training processing regimen that may be employed to train in the field for a medication not previously trained by the system. While it is contemplated that such training take place by a user, any entity may perform such training. Therefore, as is shown in FIG. 3, at step 310, a medication identifier may be provided to the imaging system, such as a label, barcode or the like. A user may be prompted to show medication packaging with a name or other indicator thereon, barcoding on the packaging, an original medication prescription, or other identification information which may be imaged to confirm the precise identity of the medication being trained. Cross reference to any other sources of information that may be available to confirm the identity of the medication, such as publicly available databases, regulatory check data sources and the like may also be employed. Alternatively, the user may be asked to simply provide the medication name, or other identifier. These are all employed to be sure of the medication identity. Knowing the medication identity, in addition to confirming proper usage, allows for mini-training data from multiple sources to be combined and provide a more robust model of the medication subject to the mini-training process. At step 320, it is asked whether the current medication to be employed by the user has been trained on the system. If so, then a record is noted in the system that the medication to be used by the particular user is one of the trained medications at step 330.

If at step 320 it is determined that the current medication has not yet been trained, processing then proceeds to step 340 where a mini-training sequence is employed. During such a mini-training sequence, the user is asked to show the medication to the imaging apparatus. The user may be guided through a short set of movements to allow for the view of the medication by the imaging apparatus. These movements may be designed to provide a best view of the medication for identification, or may mimic the steps a user may be asked to perform when actually administering their medication. The user may be asked, for example, to show the medication in their mouth or other location mimicking ingestion or other administration of the medication. Thus, by asking the user to perform these actions, during future medication administration sequences, it may be easier to identify the medication, even if partial viewing of the medication, or if the medication is not stable in a field of view due to shaking, etc., is all that is available. Consistent finger/pill interactions may also be employed to confirm color of the pill and the identity of a user, if appropriate. Instructions guiding the user through the desired movements may be displayed on a display, such as a display associated with the imaging apparatus, and possibly as shown in accordance with FIG. 1. The imaging apparatus may also employ a strobe, illuminate the display, or otherwise control an imaging area environment in order to acquire any number of desired images of the current medication. It is further contemplated in accordance with one or more embodiments of the invention that one or more initial images may be employed to make an initial determination of whether the medication can be sufficiently imaged and differentiated from other medications. This information may be further employed to monitor or modify the mini-training sequence to further allow for medication differentiation. Multiple versions of a particular medication may be requested to be imaged to account for any variation in the appearance of the medication.

Thus, the stored mini training data may comprise one or more images or video taken of a medication in one or more scenarios. These images or other mini training data may be preprocessed, such as by modifying color, modifying highlights, shadows, etc., cropping images to better present relevant portions thereof, the cropping being performed manually or automatically through feature recognition or other process. The medication may also be labeled and/or confirmed to be a correct medication. Thus, during one or more training sessions, a user or other individual may be asked to manipulate or otherwise hold a pill or other medication in a particular manner. If such a medication does not appear to be consistent with one or more prior medication identification training sessions, the user may be asked to confirm that a medication is in fact correct. The user may further be asked, through a standard input device or touch screen, to identify the medication on the display of the device. This information provided by the user may be stored with the imaging mini training data, and thus allow for additional information to be employed when training the system, thus aiding in improving the accuracy of the system. If a large number of users are performing a mini training sequence on a particular medication, the system may correlate the medications based upon these user identifications, thus allowing for a higher number of training data to be employed. Thus, feedback provided by a large number of users may be employed to further adjust and assist with future visual recognition of medication. Further, if a medication is identified by type, outliers in imaging characteristics may indicate an improper medication being used, improper lighting or the like. Thus, the system may only accumulate data for images that are at least somewhat similar in one or more dimensions to an average set of characteristics over time. Rejected or outlier images may also be manually reviewed to confirm identity, thus improving the ability to recognize medications in the future. Additionally, if particular medications are classified differently by the system, or a same identified medication is found to have different visual characteristics, manula review may be further required. If a particular user is an outlier, consistent outlier status may indicate a problem with a lighting environment, a miscalibration of a camera, or a failure by the user to follow the instruction prompts for pill training or use. Consistant poor performance may result in very little weight given to the input images from this user.

Once the appropriate number and types of images are acquired, at step 350 processing may proceed to determine on any number of dimensions a relationship between the current medication, and one or more medications previously trained on the system. Preferably, a determination may be made as to a medication trained on the system that is closest to the current medication in the most number of relevant dimensions, but any trained medication may be employed. During such process, a reference set of transformations along the relevant dimensions may be determined and stored at step 360. This transformation data is designed to convert an imaged medication to most closely resemble one of the medications that have been trained on the system. The transformation may also include variables related to environmental factors or the like that may allow for real-time adjustments of the transformations to account for current environmental factors or the like. The transformation may also account for the performance of one or more gestures or administration steps in order to further improve future recognition of the medication. After storage of such transformation data, processing ends.

Figure 4:
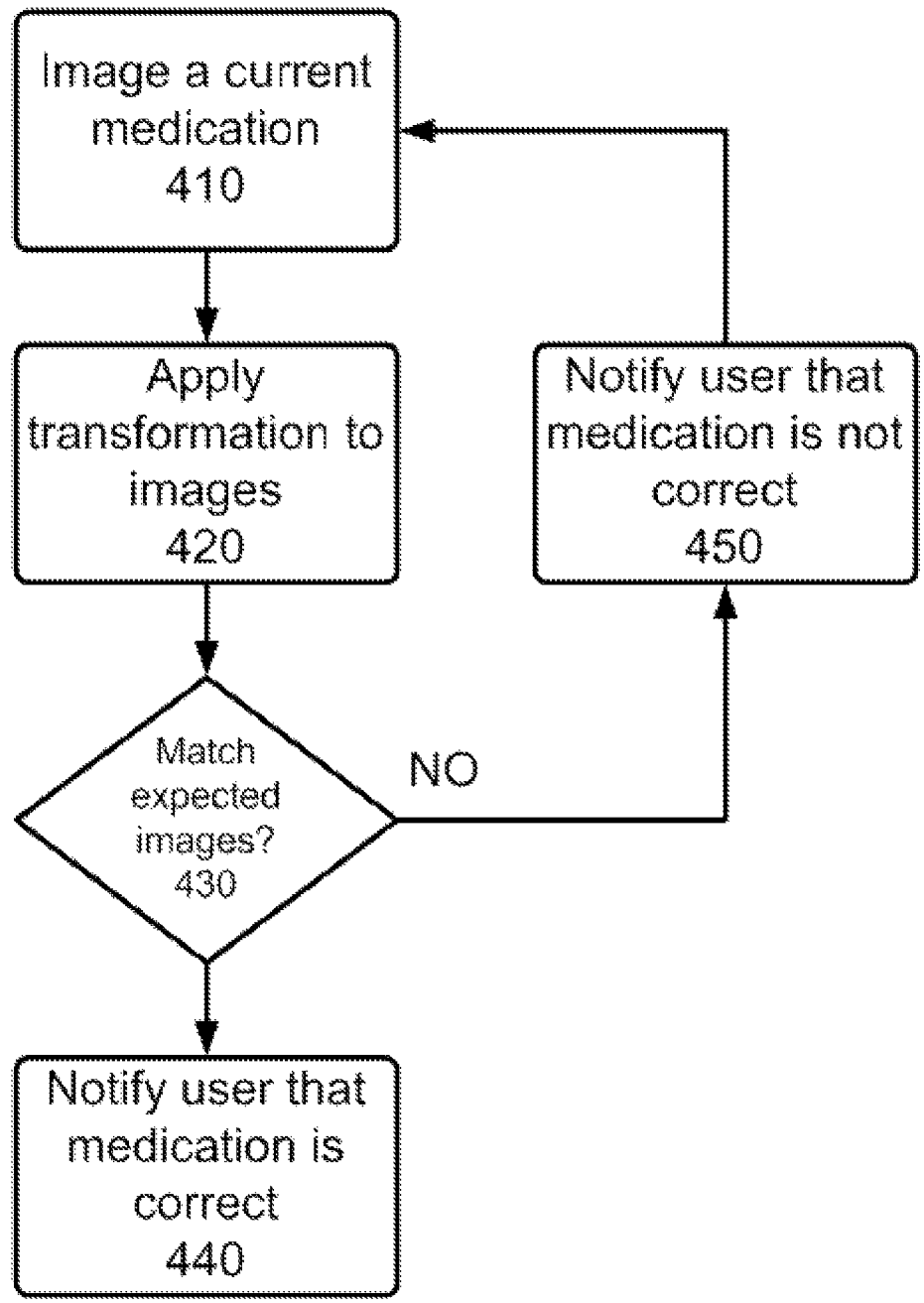
FIG. 4 is a flowchart diagram depicting use of the recognition system in accordance with an embodiment of the invention.

Upon use of the system by a user after training has been performed, the stored transformation data may be employed when trying to recognize a current medication. Thus, as shown in FIG. 4, at step 410 a current medication is preferably imaged by the imaging apparatus, preferably in response to a prompt by the system for the user to show the medication to the imaging apparatus. If the user improperly follow the prompts, real-time feedback may be provided to the user, and a different set of visual instructions may be provided in order to assist the user in properly performing the correct desired behavior. If the system is aware of the medication to be shown (either because the prescription is for one medication, or because of multiple medications one has been prompted), at step 420 a relevant transformation data is retrieved and applied to the one or more images provided by the imaging apparatus. Once applied to transform the images, at step 430 these transformed images are compared to the expected images for the particular medication to determine whether the current medication is the correct medication. If the transformed images match the expected images, and it is therefore determined that the current medication matched the expected medication, at step 440 the user is informed that the medication is correct. If the transformed images do not match the expected images, processing may pass to step 450 and the user is informed that the medication is not correct. Alternatively, the stored medication images may be transformed in accordance with the stored transformation, and then the acquired image may be directly compared with the transformed stored image. Such an alternative processing step would have the effect of increasing the reference medication library, with the caveat that if one particular reference image is improperly captured, all images referring thereto may also be improperly defined. Processing may then return to step 410 to acquire additional images of the current or another medication presented by the user. After a predetermined number of failures, the user may be asked to not take the presented medication, to call their doctor or pharmacist, or the like.

In accordance with one or more embodiments of the invention, application of transformation data to the one or more images may be modified in accordance with one or more environmental or other factors. For example, if the system is able to determine that lighting is low, the transformation data may be modified to account for the low light before application. Similarly, if the system is able to determine that the color of the ambient light is not white, various other corrections to the transformation data may be applied. In this manner, various different applications of the transformation data may be able to allow for a closer match of the transformed images to one or more of the stored medication training data.

Pill identification may also be aided through context based recognition. Thus, a particular user taking one type of medication may be most likely to be taking another type of medication. Thus, if the system is confused between two possible medication identifications, such contextual information may be employed to aid in such a determination. Other contextual information, such as time of day, number of pills, label on a pill bottle, user's identity, consistency of location of the user, etc. may be employed to further aid in pill or other medication identification.

Furthermore, data acquired by the system during the mini training process may be employed to improve the accuracy of the identification process. The acquired data may be employed to further tweak or adjust the transformation to allow for the updating and/or adjustment as more data is able to be employed. This information will thus allow for the improvement of the system and the increasing of the accuracy of the system as a whole.

The method may be implemented on a general purpose computer, a purposefully built system, or any other computing system including one or more non-transitory computer readable storage medium. Various communication systems may be employed, such as wifi, cellular or other private network. The computing system may be a local device including processor, memory, camera and display. Alternatively, one or more of these elements may be located at a remote location, such as employing cloud storage and/or processing.

The system may be further applied to any type of visual recognition system, such as facial recognition or the like. The system may also be applied to voice or other sound recognition, thus allowing for a number of reference sounds to be trained, and other sounds to be indexed therefrom in the manner as described above.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description and the following claims are intended to cover all of the generic and specific features of the invention herein described and all statements of the scope of the invention which, as a matter of language, might be said to fall there between.

What is claimed:

1. A method for training a medication identification apparatus, comprising the steps of:
    defining one or more predetermined medications;
    teaching a visual recognition system of a medication identification apparatus to recognize each of the one or more predetermined medications;
    presenting a first new medication to the medication identification apparatus to be imaged thereby;
    determining a transformation from one of the predetermined medications to the presented new first medication along one or more dimensions; and
    storing the determined transformation associated with the first new medication.

2. The method of claim 1, further comprising the step of confirming that the one or more predetermined medications cover a desired spectrum of possible new medications.

3. The method of claim 1, further comprising the step of imaging multiple versions of the first new medication to address variation therein.

4. The method of claim 1, further comprising the steps of:
    determining one or more environmental factors that may affect the teaching of the visual recognition system to recognize each of the one or more predetermined medications; and
    adjusting the parameters of the recognition of the one or more predetermined medications in accordance with the one or more determined environmental factors.

5. The method of claim 1, further comprising the steps of:
    determining one or more environmental factors that may affect the imaging of the first new medication by the medication identification apparatus; and
    adjusting the parameters of the transformation in accordance with the determined one or more environmental factors.

6. The method of claim 5, further comprising the step of providing illumination from the medication training apparatus to overcome one or more determined environmental factors.

7. The method of claim 1, wherein the visual recognition system of the medication training apparatus is located at a remote location to the medication training apparatus.

8. The method of claim 1, wherein the step of presenting the first new medication further comprises the step of performing one or more predetermined movements with the first new medication as directed on a display of the medication identification apparatus.

9. The method of claim 1, wherein the determined transformation is stored along with the one of the predetermined medications.

10. The method of claim 1, wherein the determined transform is applied to the one of the predetermined medications and stored as the first new medication.

11. The method of claim 1, wherein the one or more predetermined medications comprises the predetermined medication having a closest match with the first new medication along the one or more dimensions.

12. The method of claim 1, further comprising:
    presenting a second medication to the medication identification apparatus, the medication identification apparatus adapted to visually image the presented second medication;
    visually imaging the presented second medication;
    applying a predetermined transformation stored with a previously-imaged medication to the visually imaged presented second medication, the predetermined transformation adjusting one or more parameters of the visually imaged presented second medication along one or more dimensions; and
    comparing the transformed visually imaged second medication to a previously imaged medication in a medication library associated with the applied predetermined transformation to determine a closest match therebetween.

13. The method of claim 12, further comprising the steps of:
    determining one or more environmental factors that may affect the imaging of the presented medication by the medication identification apparatus; and
    adjusting the parameters of the transformation in accordance with the determined one or more environmental factors.

14. The method of claim 13, further comprising the step of employing a light associated with the medication identification apparatus if it is determined that such use may improve the determined one or more environmental factors.

15. The method of claim 12, further comprising the step of presenting one or more visual prompts to a user to perform one or more predetermined motions when presenting the medication to the medication identification apparatus.

16. The method of claim 15, further comprising the step of providing immediate visual feedback to the user if it is determined that the user has not properly followed the one or more visual prompts, and therefore has not properly presented the medication.

17. The method of claim 12, further comprising employing the imaged presented medication data to further adjust the predetermined transformation.

18. A system for identifying medication, comprising:
    a medication library stored to a non-transient computer readable storage medium, the medication library being formed by:
    defining one or more predetermined medications;
    teaching a visual recognition system of a medication identification apparatus to recognize each of the one or more predetermined medications;
    storing visual recognition data for each of the one or more predetermined medications to the medication library;
    presenting one or more new medication to the medication identification apparatus to be imaged thereby;
    determining a transformation from one of the predetermined medications to each of the one or more presented new medications along one or more dimensions; and
    storing the determined transformations associated with the new medication to the medication library; and
    the medication identification apparatus adapted to: visually image a medication presented thereto; apply a predetermined transformation from the medication library to the visually imaged presented medication, the predetermined transformation adjusting one or more parameters of the visually imaged presented medication along one or more dimensions; and compare the transformed visually imaged medication to one or more of the predetermined medications stored in the medication library to determine a closest match therebetween.

19. The system of claim 18, wherein the medication identification apparatus further determines one or more environmental factors that may affect the imaging of the presented medication by the medication identification apparatus, and adjusts parameters of the transformation in accordance with the determined one or more environmental factors.

20. The system of claim 18, wherein the medication identification apparatus comprises a mobile computing device.

\* \* \* \* \*